US00PP23910P2

(12) United States Plant Patent
Smith

(10) Patent No.: US PP23,910 P2
(45) Date of Patent: Sep. 17, 2013

(54) *CHRYSANTHEMUM* PLANT NAMED 'CIFZ0033'

(50) Latin Name: *Chrysanthemum×morifolium*
Varietal Denomination: CIFZ0033

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 78 days.

(21) Appl. No.: 13/385,254

(22) Filed: Feb. 10, 2012

(51) Int. Cl.
*A01H 5/00* (2006.01)

(52) U.S. Cl.
USPC ..... Plt./293

(58) Field of Classification Search
USPC ..... Plt./293
See application file for complete search history.

*Primary Examiner* — Annette Para
(74) *Attorney, Agent, or Firm* — Joshua L. Price

(57) ABSTRACT

A new *Chrysanthemum* plant named 'CIFZ0033' particularly distinguished by the small dark red inflorescences, medium yellow-green foliage color, compact plant size and rounded habit with good stem strength, and a natural season flowering response of mid-October.

1 Drawing Sheet

Latin name of the genus and species of the plant claimed: *Chrysanthemum×morifolium.*

Varietal denomination: 'CIFZ0033'.

BACKGROUND OF THE NEW PLANT

The present invention comprises a new *Chrysanthemum*, botanically known as *Chrysanthemum×morifolium*, and hereinafter referred to by the variety name 'CIFZ0033'.

'CIFZ0033' is a product of a planned breeding program. The new cultivar has small dark red inflorescences, medium yellow-green foliage color, compact plant size and rounded habit with good stem strength, and a natural season flowering response of mid-October.

'CIFZ0033' originated from a hybridization made in February 2008 in a controlled breeding environment in a greenhouse in Amanecer, Columbia. The female parent was the unpatented, proprietary plant designated '02-M061', with larger purple inflorescences, a rounder plant habit with a little larger plant size, and a natural flowering response that is two weeks faster than that of 'CIFZ0033'.

The male parent of 'CIFZ0033' was the proprietary plant designated as 'Yobonnie', U.S. Plant Pat. No. 18,886, with a lighter shade of red inflorescence color, more disc florets, a little smaller plant size, a black cloth flowering response of 10 days faster, and a natural season flowering response that is 1 month faster than that of 'CIFZ0033'.

The resultant seed was sown and grown outdoors in October 2008 in Alva, Fla. USA.

'CIFZ0033' was selected as one flowering plant within the progeny of the stated cross in April 2009 in Alva, Fla.

The first act of asexual reproduction of 'CIFZ0033' was accomplished when vegetative cuttings were propagated from the initial selection in May 2009 in a greenhouse in Alva, Fla.

BRIEF SUMMARY OF INVENTION

Horticultural examination of plants grown from cuttings of the plant initiated in May 2009, and continuing thereafter, has demonstrated that the combination of characteristics as herein disclosed for 'CIFZ0033' are firmly fixed and are retained through successive generations of asexual reproduction.

'CIFZ0033' has not been observed under all possible environmental conditions. The phenotype may vary significantly with variations in environment such as temperature, light intensity and day length.

A Plant Breeder's Right for this cultivar was applied for in Canada on Feb. 24, 2011, No. 11-7189. 'CIFZ0033' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0033' with colors being as true as possible with an illustration of this type. The photographic drawing shows a flowering potted plant of the new variety, and a close-up of the inflorescences.

DETAILED BOTANICAL DESCRIPTION

The plant descriptions, measurements and aforementioned photographs were taken outdoors in Gilroy, Calif. in early November 2011. The plants were grown in Gilroy, Calif. in an outdoor potted plant trial in one gallon pots in full sun. These plants were approximately 9 weeks of age.

Color references are made to The Royal Horticultural Society Colour Chart (R.H.S.) 2001.

TABLE 1

DIFFERENCES BETWEEN THE NEW VARIETY 'CIFZ0033' AND A MOST SIMILAR VARIETY

| | 'CIFZ0033' | 'Yocarmella' (U.S. Plant Pat. No. 15,353) |
|---|---|---|
| Ray floret color: | Darker red | Lighter red |
| Ray floret length: | Little longer | Little shorter |
| Quantity of phyllaries: | More | Fewer |
| Plant habit in bad weather: | Plant much less apt to split | Plant more apt to split |

Plant:

*Form, growth and habit.*—Herbaceous garden-type, stems upright.

*Plant height.*—11.0 cm.

*Plant height (inflorescence included).*—15.0-16.0 cm.

*Plant width.*—About 20.0 cm.

Roots:

*Number of days to initiate roots.*—About 4 days at about 22 degrees C.

*Number of days to produce a rooted cutting.*—6-8 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 147A. Lower surface: Closest to RHS 147B.

*Mature, leaf color, upper surface.*—Closest to RHS 147A. Lower surface: Closest to RHS 147B but a little more green.

*Length.*—2.9-3.5 cm.

*Width.*—3.5-3.7 cm.

*Shape.*—Ovate.

*Base shape.*—Attenuate.

*Apex shape.*—Mucronulate.

*Margin.*—Palmately lobed; irregularly incised.

*Texture, upper surface.*—Bifid T-shaped hairs. Lower surface: Bifid T-shaped hairs.

*Color of veins, upper surface.*—Indistinct.

*Color of veins, lower surface.*—Indistinct.

*Petiole color.*—RHS 138B.

*Length.*—1.6-1.8 cm.

*Diameter.*—0.15 cm.

*Texture.*—Bifid T-shaped hairs.

Stem:

*Quantity of main branches per plant.*—About 8 at this stage.

*Color of stem.*—Closest to RHS 147A.

*Length of stem.*—6.0-7.0 cm.

*Diameter.*—0.3 cm.

*Length of internodes.*—0.5-1.0 cm.

*Texture.*—Bifid T-shaped hairs.

*Color of peduncle.*—Closest to RHS 147A.

*Length of peduncle.*—3.5-4.0 cm.

*Peduncle diameter.*—0.15 cm.

*Texture.*—Bifid T-shaped hairs.

Inflorescence:

*Type.*—Compositae, solitary decorative-type inflorescences, borne terminally above foliage, ray florets arranged acropetally on a capitulum.

*Quantity of inflorescences per plant.*—20, with about 50 buds.

*Lastingness of individual blooms on the plant.*—More than 6 weeks from first color showing.

*Fragrance.*—Slightly spicy.

Bud (just when opening/showing color):

*Color.*—Closest to RHS 187B.

*Length.*—1.3 cm.

*Width.*—1.0 cm.

*Shape.*—Oblate.

Immature inflorescence:

*Diameter.*—2.5-3.0 cm.

*Color of ray florets, upper surface.*—RHS 187A to RHS 187B. Lower surface: RHS 187B.

Mature inflorescence:

*Diameter.*—3.6-4.0 cm.

*Depth.*—1.0 cm.

*Total diameter of disc.*—0.3-0.4 cm, only on very mature inflorescences.

*Receptacle height.*—0.3-0.4 cm.

*Receptacle diameter.*—0.3-0.4 cm.

Ray florets:

*Average quantity of florets.*—About 130 in several whorls.

*Color of florets, upper surface.*—Closest to RHS 53A but much deeper and velvety looking with a spot of RHS 5D basally. Lower surface: RHS 187C.

*Length.*—1.8-2.0 cm.

*Width.*—0.4-0.5 cm.

*Shape.*—Oblong.

*Apex shape.*—Acute, a few are slightly emarginate.

*Margin.*—Entire.

*Texture, upper surface.*—Papillose. Lower surface: Papillose.

Disc florets:

*Average quantity of florets.*—7-10.

*Color of florets.*—RHS 155C with RHS 9A at the apex.

*Length.*—0.3 cm.

*Width.*—0.1 cm.

*Shape.*—Tubular, elongated.

*Apex shape.*—Acute, 5 pointed.

Phyllaries:

*Quantity.*—About 22; with about 50 more involucel bracts within the inflorescence head.

*Color, upper surface.*—RHS 137A. Lower surface: RHS 137A.

*Length.*—0.4-0.6 cm.

*Width.*—0.2 cm.

*Shape.*—Lanceolate.

*Apex shape.*—Acute.

*Base.*—Fused.

*Margins.*—Entire; some papery.

*Texture, upper surface.*—Glabrous. Lower surface: Bifid T-shaped hairs.

Reproductive organs:

*Pistil.*—1, found on both types of florets.

*Length.*—0.3 cm.

*Style color.*—RHS 1C.

*Style length.*—0.2-0.25 cm.

*Stigma color.*—RHS 6B.

*Stigma shape.*—Bi-parted.

*Ovary color.*—RHS 155C.

*Ovary length.*—0.1 cm.

*Ovary width.*—0.05 cm.

*Stamens.*—4, found on only on the disc florets.

*Color of filaments.*—RHS 155C.

*Length filaments.*—0.25 cm.

*Anther color*.—RHS 9B.

*Anther length*.—0.1 cm.

*Anther shape*.—Oblong.

*Pollen amount*.—None found.

What is claimed is:

1. A new and distinct variety of *Chrysanthemum* plant named 'CIFZ0033' substantially as illustrated and described herein.

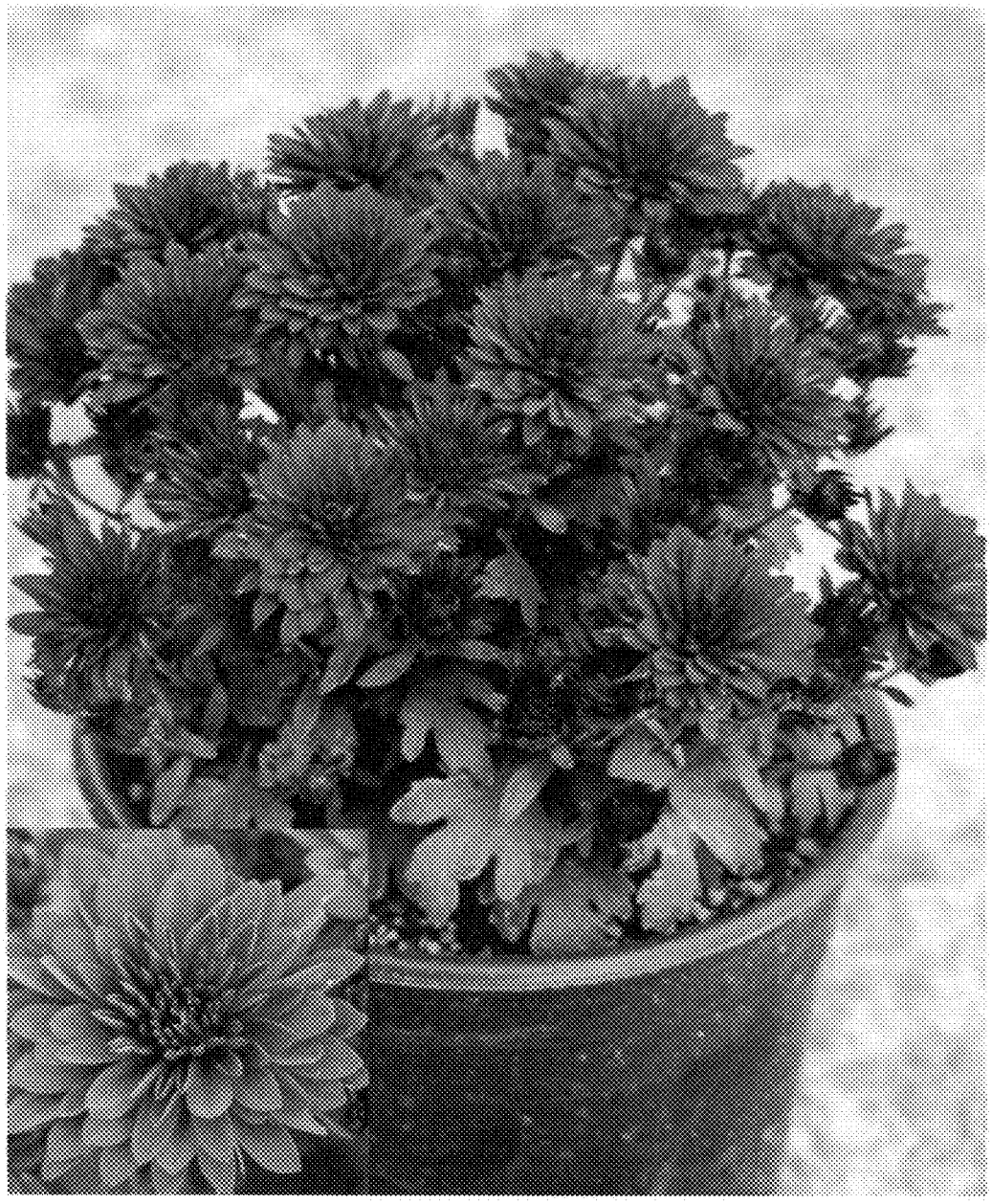

* * * * *